United States Patent

Nixon

[11] 3,967,393
[45] July 6, 1976

[54] UNDERWATER SOLIDS COLLECTING APPARATUS

[75] Inventor: Ralph Alan Nixon, Hamilton, Scotland

[73] Assignee: The Secretary of State for Trade and Industry in Her Britannic Majesty's Government of the United Kingdom of Great Britain and Northern Ireland, London, England

[22] Filed: Mar. 21, 1974

[21] Appl. No.: 453,638

[30] Foreign Application Priority Data
July 4, 1973 United Kingdom............... 31935/73

[52] U.S. Cl............................ 37/58; 37/61; 37/DIG. 8; 210/170
[51] Int. Cl.² .................................... E02F 3/88
[58] Field of Search .... 210/169, 170, 242, DIG. 21, 210/460; 61/46, 46.5; 37/58, 61, 68, DIG. 8

[56] References Cited
UNITED STATES PATENTS

| | | | |
|---|---|---|---|
| 2,897,654 | 8/1959 | Harris | 61/46 X |
| 2,988,892 | 6/1961 | Borrmann et al. | 61/46 |
| 3,091,340 | 5/1963 | Pansini | 210/169 UX |
| 3,225,930 | 12/1965 | Willinger | 210/169 X |
| 3,260,004 | 7/1966 | Brooks | 37/DIG. 8 |
| 3,360,129 | 12/1967 | Powers | 210/169 |
| 3,500,841 | 3/1970 | Logan | 210/242 X |
| 3,548,605 | 12/1970 | Paull et al. | 61/46 |
| 3,591,936 | 7/1971 | Geuns | 61/46 |
| 3,643,447 | 2/1972 | Pogonowski | 61/46 |
| 3,643,802 | 2/1972 | Jackson, Jr. | 210/460 |
| 3,683,631 | 8/1972 | McCabe | 61/46 |
| 3,686,875 | 8/1972 | Morgan | 61/46 |

Primary Examiner—Theodore A. Granger
Attorney, Agent, or Firm—Cameron, Kerkam, Sutton, Stowell & Stowell

[57] ABSTRACT

The invention concerns an apparatus for collecting solids from the bed of a liquid or for establishing an anchorage in the bed of a liquid. The apparatus comprises essentially a substantially hollow structure into which solids from the liquid bed are induced as solids in liquid suspension. In the case of the apparatus being used for the collection of solids the structure is raised to the surface of the liquid for the solids to be harvested. When the apparatus is being used as an anchoring device the design is modified such that as solids from the liquid bed are induced into the substantially hollow structure they fill or partially fill the structure when then proceeds to bury itself into the liquid bed thereby establishing an anchorage.

3 Claims, 8 Drawing Figures

UNDERWATER SOLIDS COLLECTING APPARATUS

The present invention is concerned with underwater solids collecting techniques and more particularly to underwater solids collecting apparatus. One application of the techniques and apparatus of the invention is a means for raising high density solids such as gravel in bulk from the bed of a river or a seabed, particularly in depths beyond the range of normal dredging apparatus. A further application of the techniques and apparatus of the invention is a means for establishing an underwater anchorage such as for a surface vessel or for any other structure such as a well-head.

According to the present invention an underwater solids collecting apparatus includes a substantially hollow structure submersible in a volume of liquid and having at least one intake passageway located in the lower region of the structure, the apparatus also including collection means whereby in operation liquid from the lower strata of the volume of liquid on or adjacent the bed of the liquid may be induced into the interior of the structure through the intake passageways with sufficient momentum to carry into the interior solid matter from the bed of the liquid.

Preferably the collecting means includes a vent passageway located in the upper region of the structure and through which liquid may be extracted from within the interior of the structure by suction means.

In one arrangement of the invention for the collection and harvesting of underwater solids the substantially hollow structure is in the form of a diving bell with the intake passageways extending from the lower region of the structure like peripheral legs, the structure being provided with a hopper like collecting area into which solids induced into the interior of the structure through the intake passageways may be collected.

The structure might also include an air inlet passageway through which air under pressure may be fed into the interior of the structure to act in conjunction with the vent passageway as an air-lift pump for the extraction of air/water from within the interior of the structure. With the vent passageway closed the pressurising air may with advantage be used to pressurise the structure to provide buoyancy whereby the structure will rise to the surface of the liquid.

In an alternative arrangement of the invention for establishing a means of anchorage in the bed of the liquid the substantially hollow structure includes a lower platform region with the intake passageways arranged in the base of the platform such that solids induced into the structure by the collecting means fill or substantially fill the interior of the platform region and cause it to become at least partially buried in the bed material.

In order that the present invention may be more fully understood two embodiments thereof will now be described by way of example only with reference to the accompanying drawings which illustrate vertical sections through the apparatus of the invention. FIGS. 1, 2, 3 and 4 show the apparatus of the invention as applied to the collection and harvesting of underwater solids and FIGS. 5, 6, 7 and 8 show an apparatus of the invention as applied to the establishment of an underwater anchorage.

Figure 1:
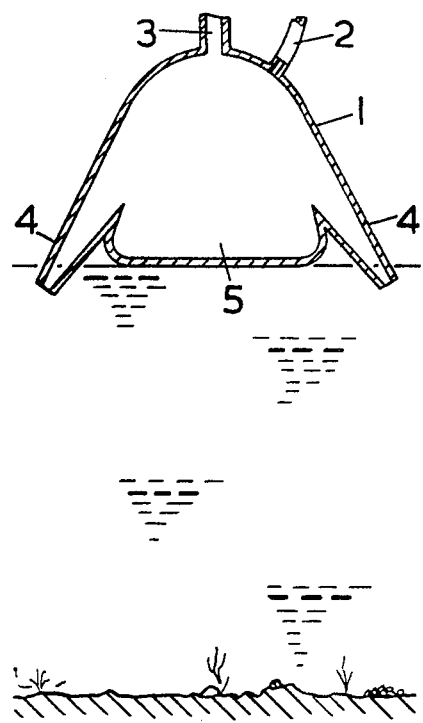
FIG. 1 shows the empty underwater solids collecting apparatus on the surface.
Figure 2:
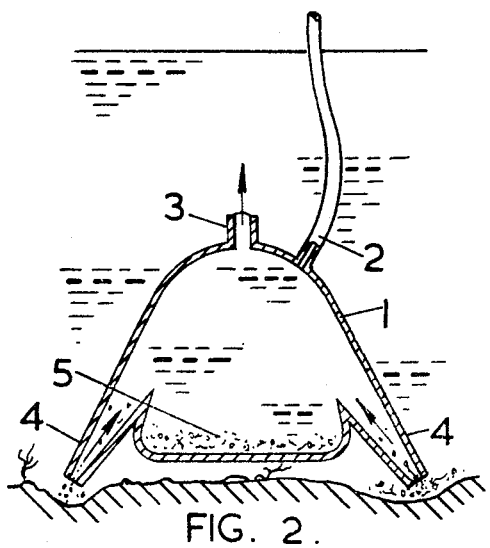
FIG. 2 shows the underwater solids collecting apparatus submerged and resting on the liquid bed.
Figure 3:
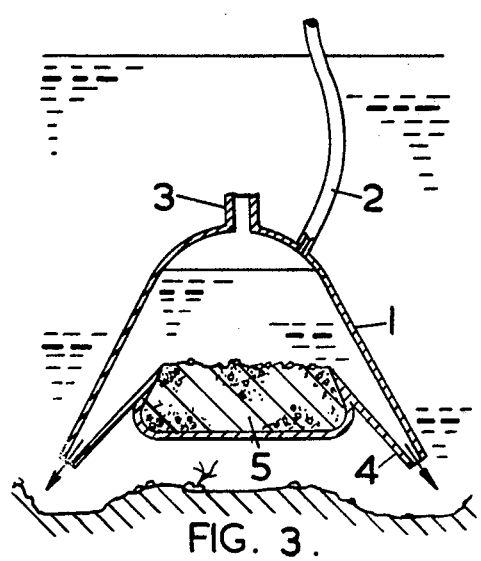
FIG. 3 shows the submerged underwater solids collecting apparatus loaded.
Figure 4:
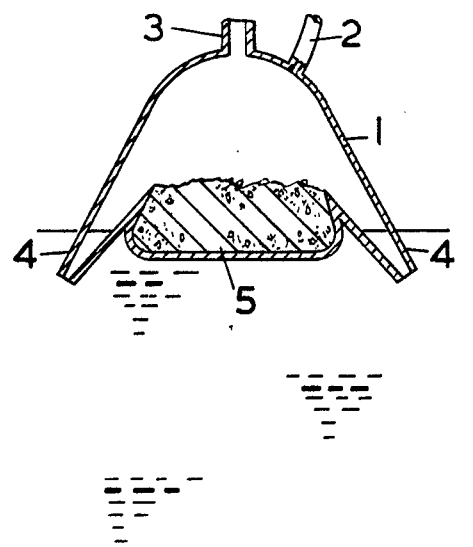
FIG. 4 shows the refloated loaded underwater solids collecting apparatus.

Referring firstly to FIGS. 1, 2, 3 and 4 the underwater solids collecting apparatus 1 floats on the surface of the liquid as shown in FIG. 1, until it is located above the site from which solids are to be recovered. The apparatus 1, which resembles the shape of an enclosed diving bell, is then flooded and sinks to the liquid bed, as shown in FIG. 2. Air, at a pressure appropriate to the depth, is pumped into the upper part of the apparatus via an inlet passageway 2 in such a manner that it passes out through a vent extraction passageway 3 in the upper part of the apparatus to form an air-lift pump whereby liquid from within the apparatus 1 is caused to rise up through the vent passageway 3 and thereby induce liquid into the vessel through open intake passageways 4 located in the lower part of the apparatus 1. The momentum of the liquid entering through the intake passageways 4 is arranged to be sufficient to carry over solids from the bed of the liquid, with which the external portions of the intake passageways 4 are in contact or adjacent to, and these solids settle out into a hopper portion 5 of the apparatus 1, excess liquid being passed out through the vent passageway 3. As shown in FIGS. 1–4, the lower ends of intake passageways 4 are positioned below the closed bottom of hopper portion 5, while the upper ends of said passageways are above the solids collecting area provided by hopper 5. With this arrangement of the intake passageways, when the flow of liquid and suspended bed material upwardly through the passageways reaches the upper ends of said passageways, the momentum of said flow is reduced so that the bed material drops into the collecting area of hopper 5 while the liquid continues upwardly to the vent passageway 3. When the hopper 5 is loaded with solids as shown in FIG. 3, the vent passageway 3 is closed and air is continued to be pumped into the apparatus 1, driving out liquid through the intake passageways 4 until the apparatus 1 becomes buoyant and rises to the surface of the liquid as shown in FIG. 4.

By this means, solids may be collected in bulk from the seabed or the bed of a river into an apparatus using only a small compressed air power input, the apparatus being raised to the surface by means of buoyancy. Only one power supply — compressed air — is required, and this can be supplied to the apparatus through flexible pipework. Wear of parts is small since the solids only move rapidly relative to boundary surfaces through the intake passageways from the bed of the liquid to the hopper contained within the apparatus. The loaded refloated apparatus can be detached from the compressed air supply and taken to an offloading station without interrupting the raising of the solids using the next empty apparatus, once it in turn has been connected to the compressed air supply. The shape and size of the apparatus is not limited to the form shown in the accompanying drawings, which illustrate only the principle of the collecting cycle. The apparatus could be left at one point on the bed of liquid until loaded or it could be moved about the bed whilst loading, according to the nature of the deposits. Air is only one example of the pumping means by which solids are induced into the vessel. A jet pump, or a centrifugal pump, could also be employed for this purpose, and, in this case, a liquid supply for the jet pump and a supply of electricity for the centrifugal pump would be needed in addition to the air supply required to give the apparatus buoyancy.

Figure 5:
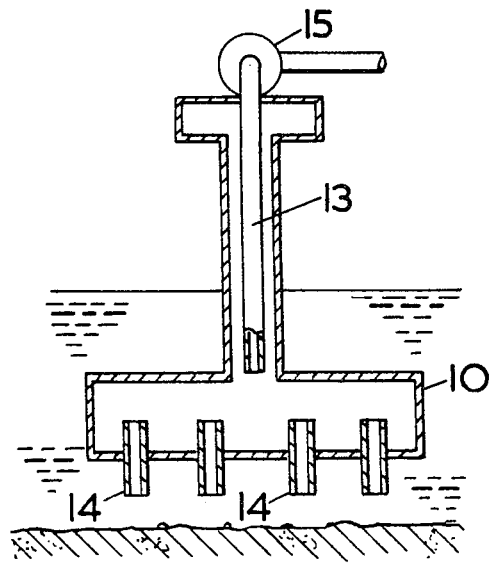
FIG. 5 shows the anchoring apparatus on the surface.
Figure 6:
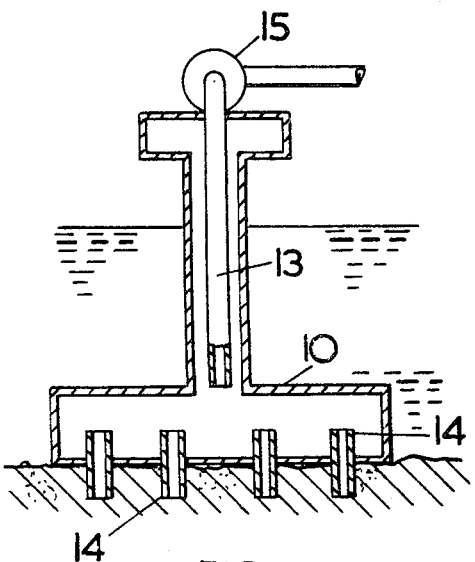
FIG. 6 shows the flooded anchoring apparatus submerged and resting on the liquid bed.

Referring now to FIGS. 5, 6, 7 and 8 the underwater anchoring apparatus in the form of a hollow structure 10 floats on the surface of the liquid as shown in FIG. 5 until it is located above the site where it is to be anchored. The hollow structure 10 is then flooded and sinks to the liquid bed as shown in FIG. 6. The liquid contained within the structure is then expelled in any one or more of a number of ways; for example, by connecting the interior of the structure to the suction pipe of a pump, either submerged or mounted above the surface of the liquid, or by a water jet ejector, or by an air-lift pump.

Figure 7:
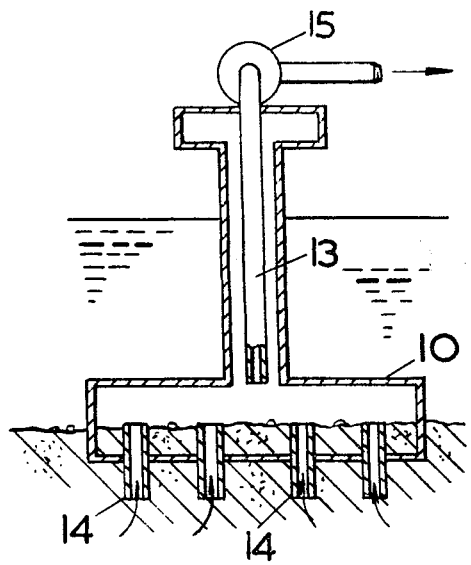
FIG. 7 shows the submerged anchoring apparatus being evacuated of water, which is being replaced by material from the liquid bed.
Figure 8:
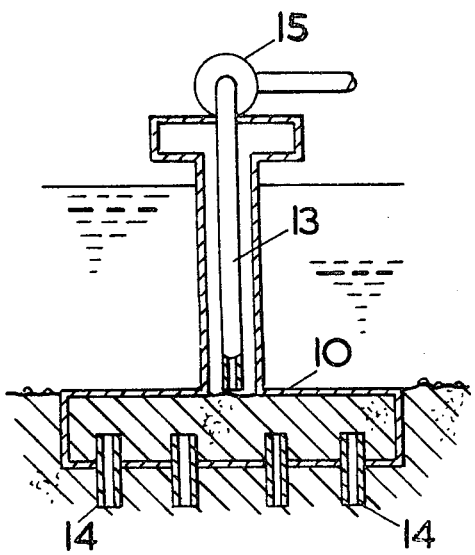
FIG. 8 shows the anchoring apparatus partially buried in the liquid bed thereby providing a secure anchorage.

As shown in FIG. 7 the liquid within the hollow structure 10 is expelled through a pipe 13 connected to a submerged pump 15 whereby liquid is induced into the structure through open intake passageways 14 located in the lower region of a platform-like lower portion of the structure 10. The momentum of the liquid entering through the intake passageways 14 is arranged to be sufficient to carry over solids from the liquid bed, with which the external portions of the intake passageways 14 are in contact or are adjacent to, into the interior of the structure 10. The velocity within the structure 10 is arranged to be sufficiently low for heavy solids to settle out of suspension once they have entered the structure through the intake passageways 14. This action continues with the platform-like lower portion of the structure 10 gradually filling with material from the liquid bed and at the same time being buried deeper in the liquid bed to form a firm anchorage. If the means for expelling the liquid from the interior of the structure is able to handle solids then the process can continue after the structure 10 is full of solid material from the liquid bed, excess solid material passing out through the pipe 13 and the pump 15 and settling on top of the structure which continues to bury itself, thereby increasing the effectiveness of the structure as an anchorage.

One advantage of using this method to establish an anchoring point is that comparatively little material need be used to construct the structure, the majority of the mass of the anchoring device being provided by the material dredged up from the liquid bed. The actual size of the anchorage may vary enormously as the artisan skilled in the art will readily appreciate. At one extreme the anchorage might for example be used to provide a secure mooring for a small boat while at the other extreme the anchorage might constitute for example the whole or a substantial part of an oil rig platform.

I claim:

1. Underwater solids collecting apparatus for harvesting in bulk bed material from the bed of a volume of liquid comprising a substantially hollow structure submersible in said volume of liquid and having a closed solid bottom portion forming a hopper-like collecting area in which bed material may be collected, at least two intake passageways located in the lower regions of said structure with at least one on each side of said closed bottom portion, an extraction passageway communicating directly with and continuously open to the upper portion of said structure; said apparatus also including an air inlet passageway connected to the upper portion of said structure adjacent but laterally offset from the extraction passageway through which air under pressure is fed into the interior of said structure continuously during use of the apparatus, said air being extracted from the interior of said structure through said extraction passageway thereby inducing into the interior of said structure through said intake passageways liquid from the lower strata of said volume of liquid, said liquid being induced into said interior with sufficient momentum to carry into said interior solid material from the bed of said volume of liquid, said induced liquid being extracted from said hollow structure along with said air through said extraction passageway and said solid material being deposited in said hopper-like collecting area between said intake passageways, said substantially hollow structure being, in section at least, in the general form of a diving bell with said intake passageways extending downwardly from the lower region of said bell like peripheral legs, each leg having an inlet opening at its lower end positioned below the closed bottom portion of said structure and communicating with an upwardly extending passageway having an outlet opening at its upper end in communication with the interior of said bell above said hopper-like collecting area.

2. Underwater solids collecting apparatus as claimed in claim 1 in which means are provided to close the extraction passageway while continuing to supply air under pressure to said structure through said air inlet passageway to drive liquid out through said intake passageways to achieve a degree of buoyancy in said structure whereby said structure may be raised to the surface of said volume of liquid.

3. Underwater solids collecting apparatus as claimed in claim 1 in which said extraction passageway is connected with pump apparatus operative in use to extract liquid from within said substantially hollow structure.

* * * * *

UNITED STATES PATENT OFFICE
CERTIFICATE OF CORRECTION

Patent No. 3,967,393          Dated July 6, 1976

Inventor(s) Ralph Alan Nixon

It is certified that error appears in the above-identified patent and that said Letters Patent are hereby corrected as shown below:

Cover page, delete: "[73] Assignee:
The Secretary of State for Trade and Industry
in Her Brittanic Majesty's Government of
the United Kingdom of Great Britain and
Northern Ireland, London, England", Signed and Sealed this Seventh Day of June 1977

[SEAL]

*Attest:*

RUTH C. MASON
*Attesting Officer*

C. MARSHALL DANN
*Commissioner of Patents and Trademarks*